United States Patent
Okaniwa

(10) Patent No.: US 9,192,288 B2
(45) Date of Patent: Nov. 24, 2015

(54) ENDOSCOPE

(71) Applicant: OLYMPUS CORPORATION, Tokyo (JP)

(72) Inventor: Suguru Okaniwa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 224 days.

(21) Appl. No.: 13/654,828

(22) Filed: Oct. 18, 2012

(65) Prior Publication Data

US 2013/0041224 A1 Feb. 14, 2013

Related U.S. Application Data

(63) Continuation of application No. PCT/JP2011/059788, filed on Apr. 21, 2011.

(30) Foreign Application Priority Data

Apr. 26, 2010 (JP) ................................. 2010-101273

(51) Int. Cl.
  *A61B 1/00* (2006.01)
  *A61B 1/005* (2006.01)
  *G02B 23/24* (2006.01)

(52) U.S. Cl.
  CPC ............. *A61B 1/0055* (2013.01); *A61B 1/0056* (2013.01); *G02B 23/2476* (2013.01)

(58) Field of Classification Search
  CPC ...... A61B 1/0055; A61B 1/008; A61B 1/0056
  USPC .................................. 600/130, 139–146, 149
  See application file for complete search history.

(56) References Cited

U.S. PATENT DOCUMENTS 8,206,287 B2 * 6/2012 Matsuo .......................... 600/140
2007/0225563 A1 * 9/2007 Ogino ........................... 600/130

FOREIGN PATENT DOCUMENTS

| EP | 1 849 396 A1 | 10/2007 |
|---|---|---|
| JP | 2004-141366 | 5/2004 |
| JP | 2006-218231 | 8/2006 |
| JP | 2007-252447 | 10/2007 |
| WO | WO 2006/085620 A1 | 8/2006 |

* cited by examiner

*Primary Examiner* — Thomas J Sweet
*Assistant Examiner* — Rajaa El Alami
(74) *Attorney, Agent, or Firm* — Scully, Scott, Murphy & Presser, PC

(57) ABSTRACT

An endoscope includes an active bending portion provided in an insertion portion and bendable according to a bending operation, the active bending portion including bending pieces adjacent to each other and pivotably connected together via a plurality of rotation shafts, the rotation shafts being located at positions differing by 90° in a circumferential direction J of the bending pieces, and a passive bending portion provided closer to the proximal end side than the active bending portion and passively bendable when an external force is applied thereto, the passive bending portion including bending pieces adjacent to each other and pivotably connected together via a plurality of rotation shafts, the rotation shafts being located at positions differing by 60° in the circumferential direction J.

1 Claim, 18 Drawing Sheets

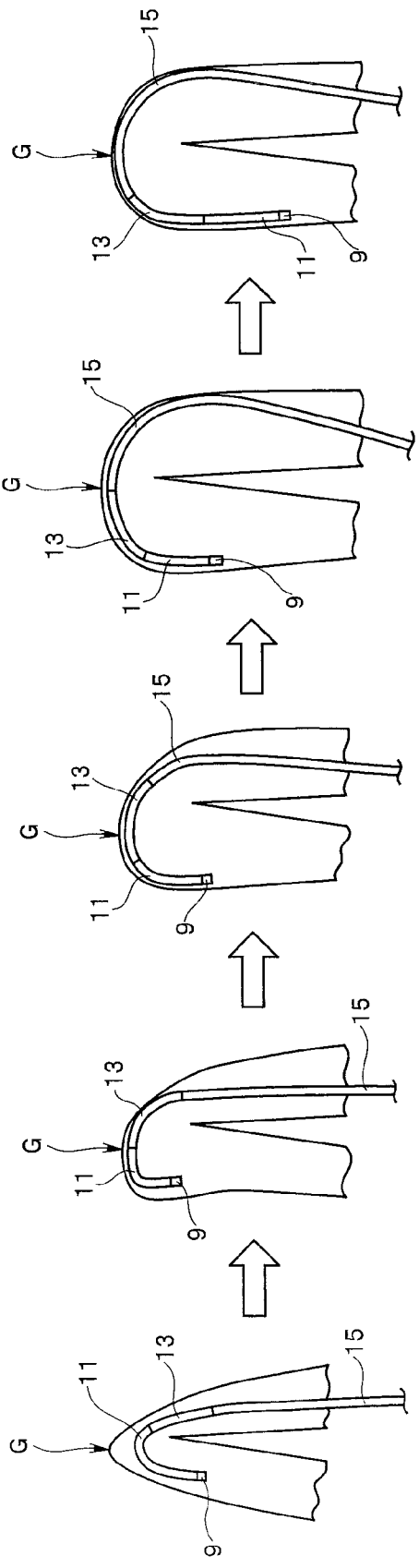

Y1=Y3

$$\text{ANGLE GAP} = \frac{1}{\cos\frac{\pi}{2n}}$$

ENDOSCOPE

CROSS REFERENCE TO RELATED APPLICATION

This application is a continuation application of PCT/JP2011/059788 filed on Apr. 21, 2011 and claims benefit of Japanese Application No. 2010-101273 filed in Japan on Apr. 26, 2010, the entire contents of which are incorporated herein by this reference.

BACKGROUND OF THE INVENTION

1. Field of the Invention

The present invention relates to an endoscope provided with an insertion portion inserted into an object or a subject.

2. Description of the Related Art

In recent years, endoscopes have been widely used in a medical field and an industrial field. Endoscopes used in the medical field can observe organs in a body cavity by inserting an elongated insertion portion into the body cavity which is a subject and perform various types of treatment using a treatment instrument inserted into an insertion channel for the treatment instrument provided for the endoscope as required.

On the other hand, endoscopes used in the industrial field can observe damage and corrosion or the like of a region to be examined of an object or perform inspections of various types of treatment by inserting an elongated insertion portion of the endoscope into the object such as a jet engine and pipes at a factory or the like.

Normally, an insertion portion of an endoscope is provided, on its distal end in an insertion direction (hereinafter simply referred to as "distal end side"), with a bending portion which is bendable by 360° in directions combining four directions; upward, downward, leftward and rightward, by pivotably connecting a plurality of bending pieces along the insertion direction, or to be more specific, bending pieces arranged adjacent to each other in the insertion direction using rivets that constitute a plurality of rotation shafts, located at positions differing by 90° in a circumferential direction of the bending pieces.

Hereinafter, the bending in the configuration in which the bending pieces are pivotably connected together using rivets that constitute a plurality of rotation shafts, located at positions differing by 90° in a circumferential direction of the bending pieces is referred to as "two-axis bending."

The bending portion is bendable in the aforementioned direction by one or a plurality of bending wires being pulled out of four bending wires inserted into the insertion portion according to bending operation by an operator. Hereinafter, the bending portion bent by the bending wires is referred to as "active bending portion."

Furthermore, there is also a known configuration provided with a passive bending portion which cannot be bent by a bending operation of the operator, but is flexible and passively bendable when an external force is applied thereto, provided closer to the proximal end side in the insertion portion (hereinafter simply referred to as "proximal end side") than the active bending portion.

For example, Japanese Patent Application Laid-Open Publication No. 2006-218231 discloses an endoscope having a configuration in which bending pieces are used in a passive bending portion and the radius of curvature of the passive bending portion is greater than the radius of curvature of an active bending portion.

The passive bending portion described in Japanese Patent Application Laid-Open Publication No. 2006-218231 conventionally also has the aforementioned configuration performing two-axis bending.

Here, FIG. 16 is a diagram schematically illustrating a distribution of maximum bending angles in the bending direction of a bending portion which performs two-axis bending. The "maximum bending angle" refers to a state in which peripheral edges of bending pieces adjacent to each other come into contact with each other and the bending thereof in the direction is regulated.

In FIG. 16, an arrow Y1 shows a maximum bending angle in an upward, downward, leftward or rightward direction, taking the upward direction as an example, an arrow Y2 shows a maximum bending angle in an intermediate direction between the upward and downward directions, and the leftward and rightward directions, taking the intermediate direction between the upward direction and leftward direction as an example. When a circle X shown by a dotted line indicates a track of an ideal maximum bending angle, the ideal for the maximum bending angle is that the maximum bending angle be the same, as illustrated with the circle X, no matter whether the bending portion is bent in the upward and downward directions or bent in the leftward and rightward directions or bent in an intermediate direction between the upward, downward, leftward and rightward directions (hereinafter referred to as "twist direction"), that is, no matter in which direction in 360° the bending portion is bent.

However, in the case of the two-axis bending, as shown in FIG. 16, it is geometrically known that the maximum bending angle of the bending in the twist direction is $1/\cos(\pi/4) \approx 1.41$ times (Y2=1.41Y1) with respect to the bending in the upward, downward, leftward and rightward directions as shown in FIG. 18, which will be described later, that is, an angle gap attributable to a difference in the maximum bending angle is generated 1.41 times.

That is, the actual track of the maximum bending of the bending portion that performs two-axis bending has a rectangular shape as shown by a solid line T1 shown in FIG. 16.

Moreover, it is necessary to reduce the difference in maximum bending angles by the bending direction, whether it is the active or passive bending portion. That is, as shown in FIG. 16, it is necessary to make the track of the maximum bending angle approximate to the circle X.

In view of the above-described circumstances, Japanese Patent Application Laid-Open Publication No. 2004-141366 discloses, as a solution to the problems of two-axis bending in the active bending portion, a configuration of an active bending portion which is bendable by 360° in directions combining four directions; upward, downward, leftward and rightward by pivotably connecting bending pieces arranged adjacently to each other in the insertion direction using rivets that constitute a plurality of rotation shafts, located at positions differing by 45° in a circumferential direction of the bending pieces.

Hereinafter, the bending in the configuration in which the bending pieces are pivotably connected together in upward, downward, leftward and rightward directions using rivets that constitute a plurality of rotation shafts, located at positions differing by 45° in a circumferential direction of the bending pieces is referred to as "four-axis bending."

Here, FIG. 17 is a diagram schematically illustrating a distribution of maximum bending angles in the bending direction of the bending portion that performs four-axis bending and FIG. 18 is a diagram illustrating an angle gap with respect to the number of bending axes.

As shown in FIG. 17, when the active bending portion has a four-axis bending configuration as described in Japanese Patent Application Laid-Open Publication No. 2004-141366, in the case of four-axis bending, a maximum bending angle Y3 (represented by a UL direction in FIG. 17) in a direction intermediate between upward and downward directions, and leftward and rightward directions (UL direction, UR direction, DL direction and DR direction) of the twist directions is equal to a maximum bending angle Y1 in upward, downward, leftward and rightward directions (Y1=Y3), and as shown in FIG. 18, a maximum bending angle Y4 (represented by a twist direction between the UL direction and upward direction in FIG. 17) in the twist direction except the UL direction, UR direction, DL direction and DR direction is geometrically known to be $1/\cos(\pi/8) \approx 1.08$ times the maximum bending angle Y1 in the upward, downward, leftward and rightward directions and UL direction, UR direction, DL direction, DR direction (represented by the downward direction in FIG. 17) and Y3 (Y4=1.08Y1(Y3)), the actual track of the maximum bending becomes an octagonal shape shown by a solid line T2 shown in FIG. 17 and approximates to the circle X, and it thereby minimizes the difference in maximum bending angles by the bending direction.

As shown in FIG. 18, the greater the number of rivets connecting the bending pieces, that is, the greater the number of bending axes, the smaller is the difference in maximum bending angles by the bending direction, and it is clear that the angle gap due to the difference in maximum bending angles of a bending portion that performs n-axis bending is $1/\cos(\pi/2n)$.

Here, FIG. 19 shows a diagram schematically illustrating the operation of raising the transverse colon using an endoscope having only an active bending portion, FIG. 20 shows a diagram schematically illustrating the operation of raising the transverse colon using an endoscope having an active bending portion and a passive bending portion, FIG. 21A shows a diagram schematically illustrating the operation of causing an endoscope having only an active bending portion to pass through the hepatic flexure of the intestine, FIG. 21B shows a diagram schematically illustrating the operation of causing an endoscope having an active bending portion and a passive bending portion to pass through the hepatic flexure of the intestine and FIG. 22 shows a diagram schematically illustrating the operation of causing an endoscope having an active bending portion and a passive bending portion to pass through the sigmoid colon of the intestine.

When performing the known operation of raising the transverse colon P using the insertion portion of an endoscope having only an active bending portion, which is normally used, it is a general practice as shown in FIG. 19 that a distal end portion 101 of an insertion portion 100 is made to pass through a descending portion N of the transverse colon P by bending an active bending portion 102 and the insertion portion is pulled back with the distal end portion 101 being hooked at the transverse colon P. After that, with the transverse colon P being raised and straightened, the insertion portion 100 is pushed in and made to move forward.

Moreover, it has been known that, as shown in FIG. 20, when an attempt is made to raise the transverse colon P using an insertion portion 200 in which a passive bending portion 203 is formed on the proximal end side of an active bending portion 202, since the passive bending portion 203 is formed to be flexible, the passive bending portion 203 is bent without raising the transverse colon P, and if the bending angle thereof becomes excessive, when the insertion portion is pulled back with the distal end portion 201 being hooked at the transverse colon, a force is applied to the distal end portion 201 in a direction opposite to the hooking direction, resulting in that the distal end portion 201 is twisted and the distal end portion 201 is unhooked.

Furthermore, as shown in FIG. 21A, also when the distal end portion 101 is made to pass through the hepatic flexure Q of the transverse colon P, in the case of a normal endoscope provided only with an active bending portion 102, the distal end portion 101 can be made to pass through the hepatic flexure Q when the distal end portion 101 has reached the flexural area of the hepatic flexure Q by rotating the insertion portion 100 counterclockwise from there. However, it has been known that, as shown in FIG. 21B, in the case of the endoscope provided with the passive bending portion 203, if the passive bending portion 203 is bent excessively, depending on the design, the distal end portion 201 does not reach the flexural area of the hepatic flexure Q.

Furthermore, it has been known that, as shown in FIG. 22, also when the insertion portion 200 passes through the sigmoid colon S, in the case of the endoscope provided with the passive bending portion 203, if the passive bending portion 203 is bent excessively, the force applying to the insertion portion 200 is inverted from S1 to S2.

SUMMARY OF THE INVENTION

An endoscope according to an aspect of the present invention includes an insertion portion inserted into a subject, an active bending portion provided in the insertion portion and bendable according to a bending operation of an operator, the active bending portion including a plurality of bending pieces arranged adjacently to each other in an insertion direction of the insertion portion which are pivotably connected to each other by a plurality of rotation shafts, the rotation shafts being located at positions differing from each other by 90° in a circumferential direction of the bending pieces, and a passive bending portion provided closer to a proximal end side in the insertion direction than the active bending portion in the insertion portion and not bendable according to a bending operation of the operator but passively bendable when an external force is applied to the passive bending portion, the passive bending portion including a plurality of bending pieces arranged adjacently to each other in the insertion direction which are pivotably connected to each other by a plurality of rotation shafts, the rotation shafts being located at positions differing from each other by 60° in the circumferential direction, wherein the active bending portion has a configuration in which the bending pieces adjacent to each other in the insertion direction are pivotably connected together via two first mutually opposed rotation shafts in upward and downward directions and pivotably connected via two second mutually opposed rotation shafts at positions differing by 90° from the first rotation shafts in a circumferential direction of the bending pieces in leftward and rightward directions, and the passive bending portion has a configuration in which the bending pieces adjacent to each other in the insertion direction are pivotably connected together via two third mutually opposed rotation shafts located coaxially with the first rotation shafts in the insertion direction, pivotably connected together via two fourth mutually opposed rotation shafts located at positions differing by 60° from the third rotation shafts in the circumferential direction and pivotably connected together via two fifth mutually opposed rotation shafts located at positions differing by 60° from the third rotation shafts and the fourth rotation shafts in the circumferential direction.

BRIEF DESCRIPTION OF THE DRAWINGS

FIG. 13A is a diagram illustrating the distal end portion of the insertion portion of the endoscope in FIG. 1 with the active bending portion being bent and made to enter into the flexural area;

FIG. 13B is a diagram schematically illustrating the insertion portion in FIG. 13A pushed in so as to press the active bending portion and the passive bending portion against the flexural area;

FIG. 13C is a diagram schematically illustrating the active bending portion which has passed through the flexural area along the wall surface of the flexural area;

FIG. 13D is a diagram schematically illustrating an intermediate state of the passive bending portion passing through the flexural area along the wall surface of the flexural area;

FIG. 13E is a diagram schematically illustrating the passive bending portion which has passed through the flexural area along the wall surface of the flexural area;

DETAILED DESCRIPTION OF THE PREFERRED EMBODIMENT

Hereinafter, embodiments of the present invention will be described with reference to the accompanying drawings. It should be noted, however, that the drawings are schematic ones, the relationship between the thickness and width of each member, the ratio of thickness among the respective members or the like are different from the real ones, and it goes without saying that different dimensional relationships and ratios among drawings are also included.

Figure 1:
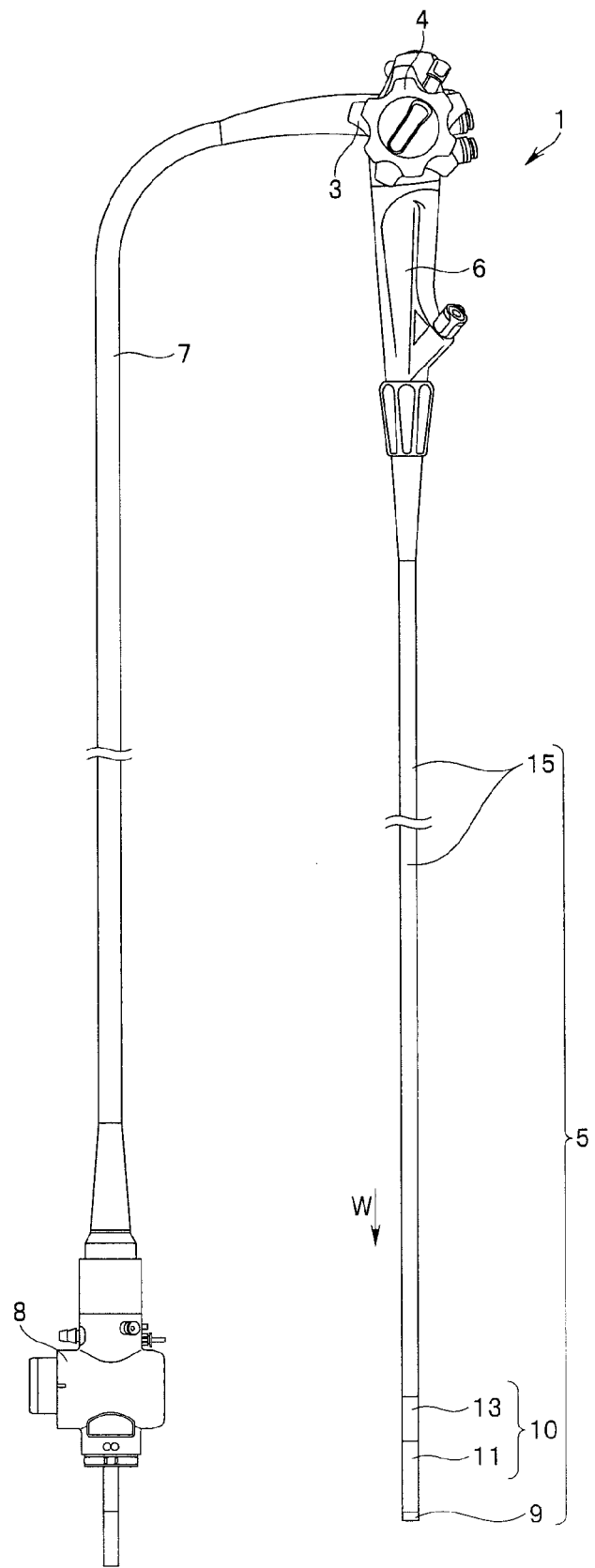
FIG. 1 is a diagram illustrating an endoscope of the present embodiment.
Figure 2:
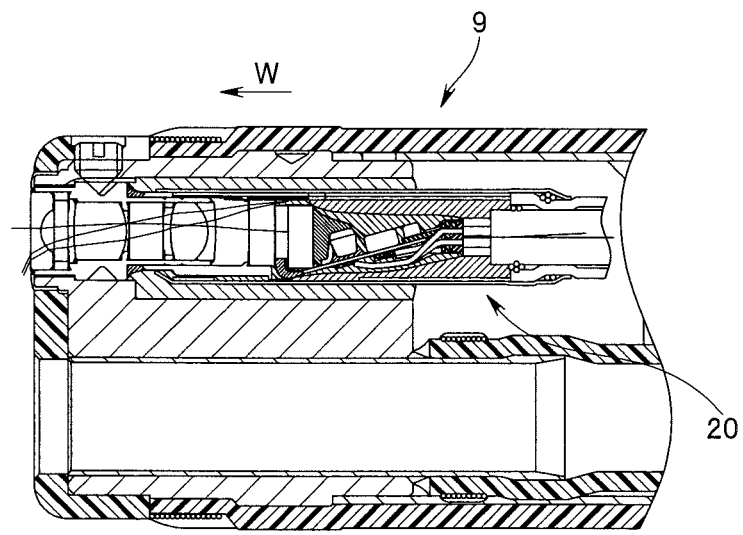
FIG. 2 is a partial cross-sectional view of a distal end portion provided at an insertion portion of the endoscope in FIG. 1.
Figure 3:
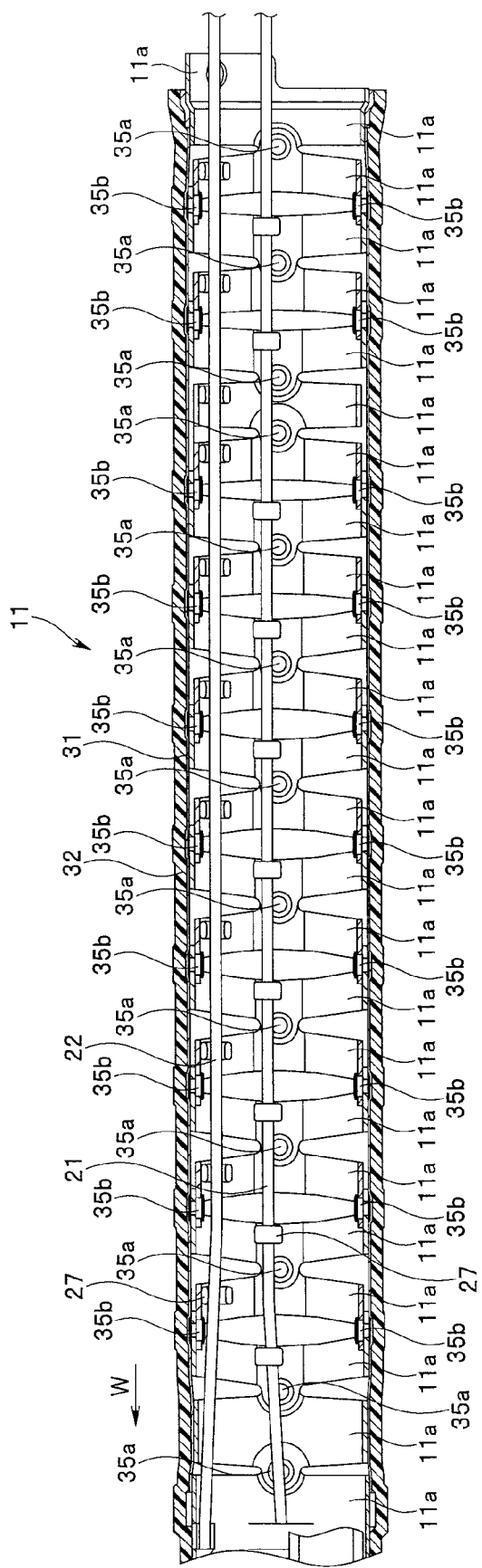
FIG. 3 is a partial cross-sectional view of an active bending portion provided at the insertion portion of the endoscope in FIG. 1.
Figure 4:
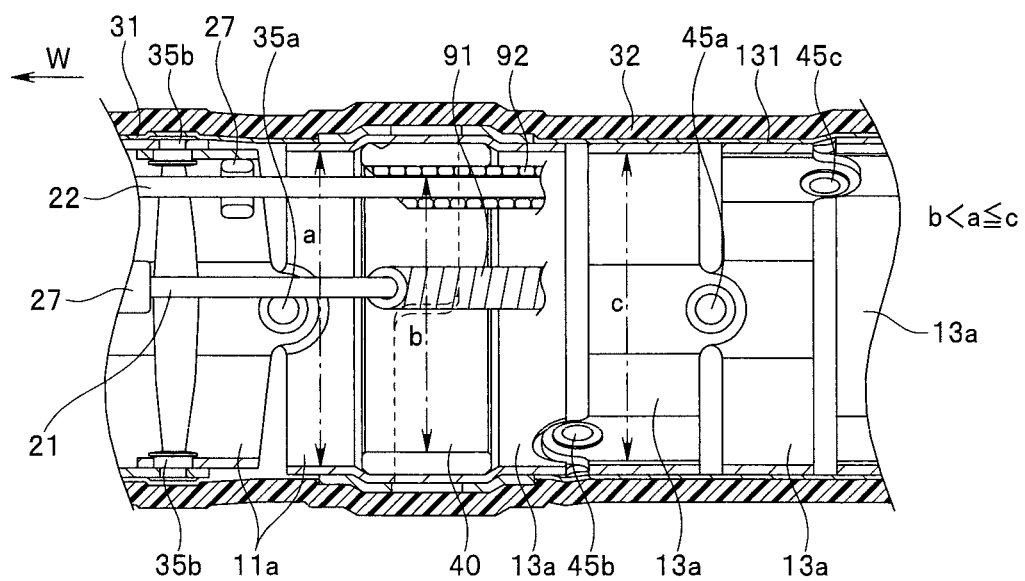
FIG. 4 is a partial cross-sectional view illustrating the vicinity of a connection region between the active bending portion and the passive bending portion provided at the insertion portion of the endoscope in FIG. 1.
Figure 5:
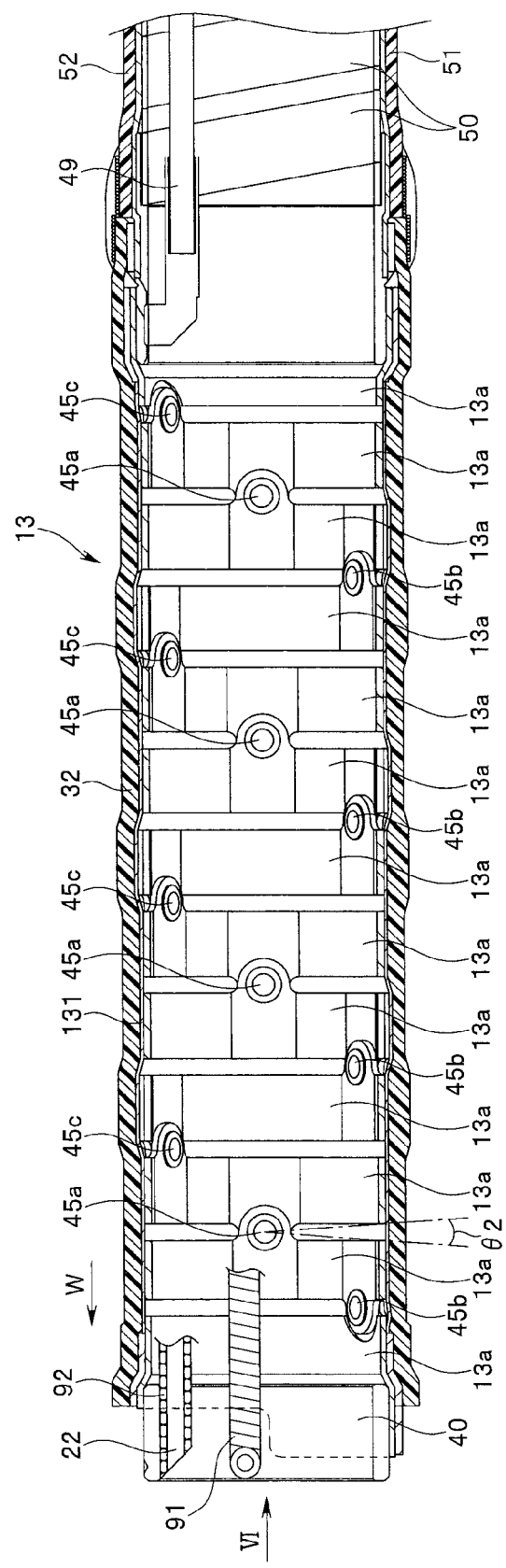
FIG. 5 is a partial cross-sectional view of the passive bending portion provided at the insertion portion of the endoscope in FIG. 1.

FIG. 1 is a diagram illustrating an endoscope of the present embodiment, FIG. 2 is a partial cross-sectional view of a distal end portion provided at an insertion portion of the endoscope in FIG. 1, FIG. 3 is a partial cross-sectional view of an active bending portion provided at the insertion portion of the endoscope in FIG. 1, FIG. 4 is a partial cross-sectional view illustrating the vicinity of a connection region between the active bending portion and the passive bending portion provided at the insertion portion of the endoscope in FIG. 1 and FIG. 5 is a partial cross-sectional view of the passive bending portion provided at the insertion portion of the endoscope in FIG. 1.

Figure 6:
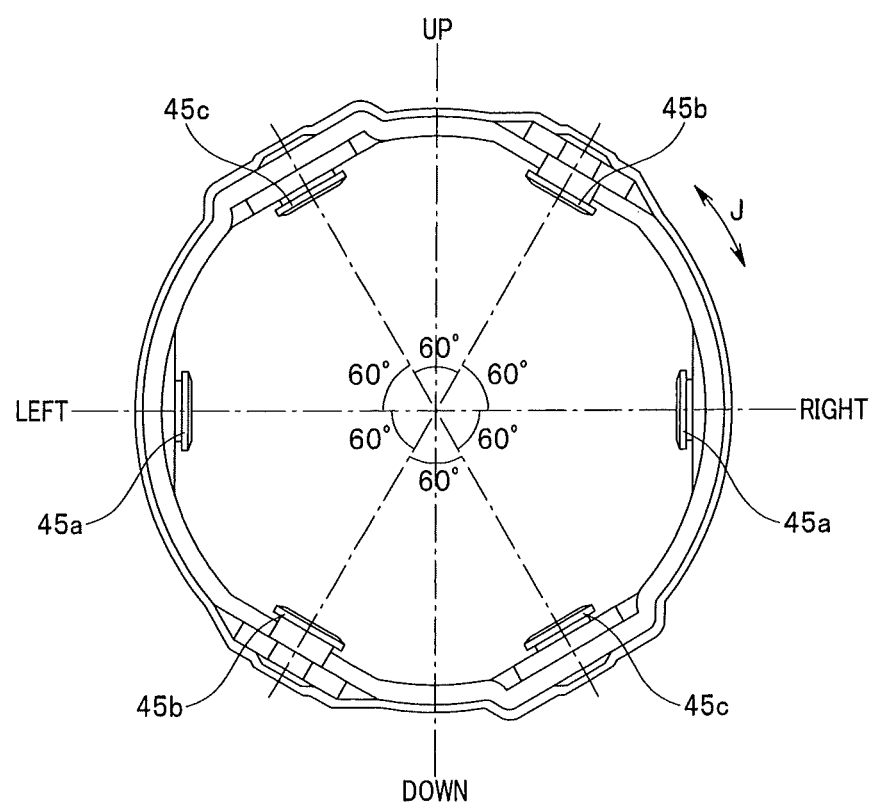
FIG. 6 is a diagram of the passive bending portion in FIG. 5 viewed from a direction VI in FIG. 5.
Figure 7:
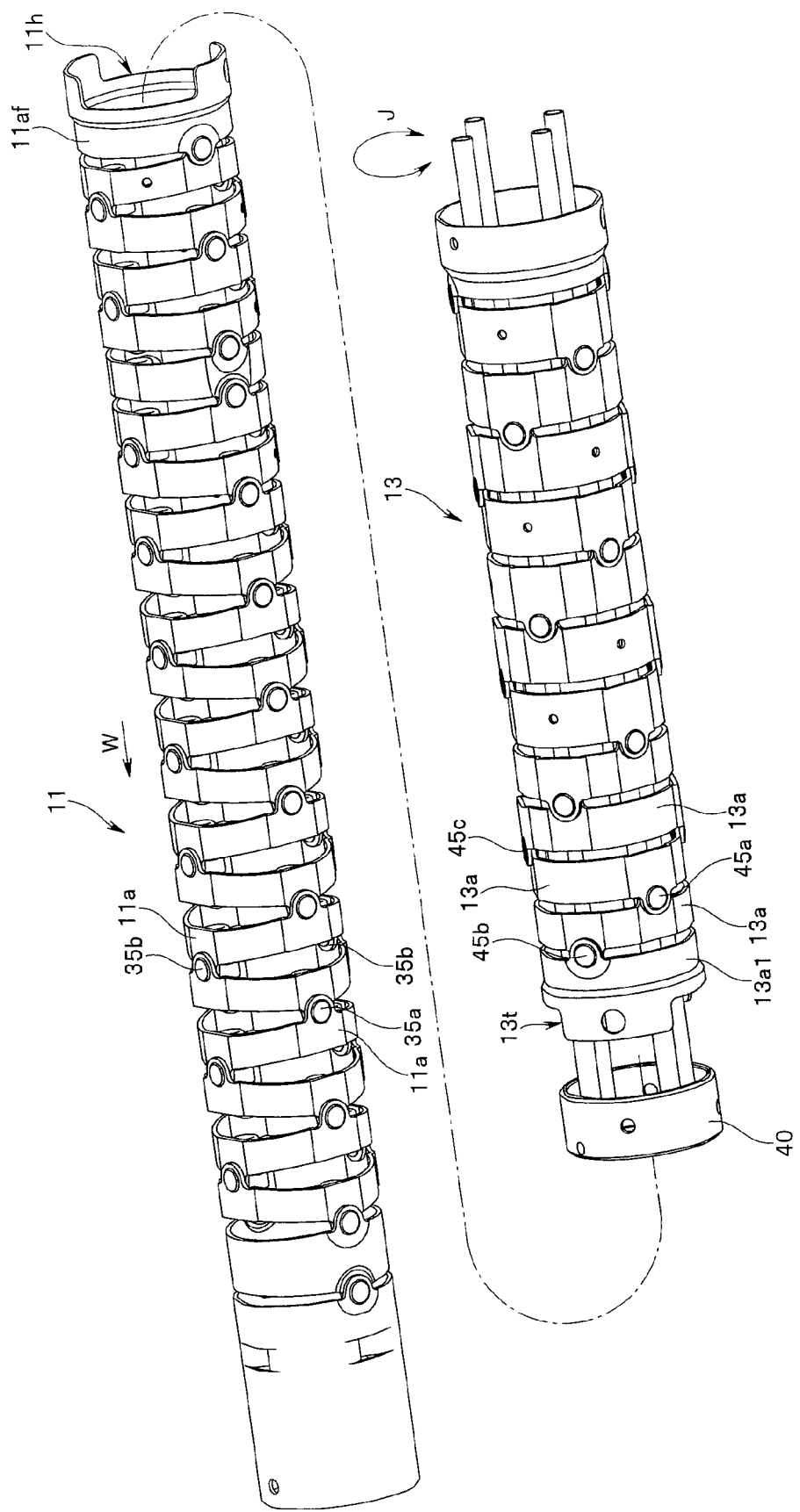
FIG. 7 is a perspective view illustrating bending pieces constituting the active bending portion and bending pieces constituting the passive bending portion provided at the insertion portion of the endoscope in FIG. 1 before connection.
Figure 8:
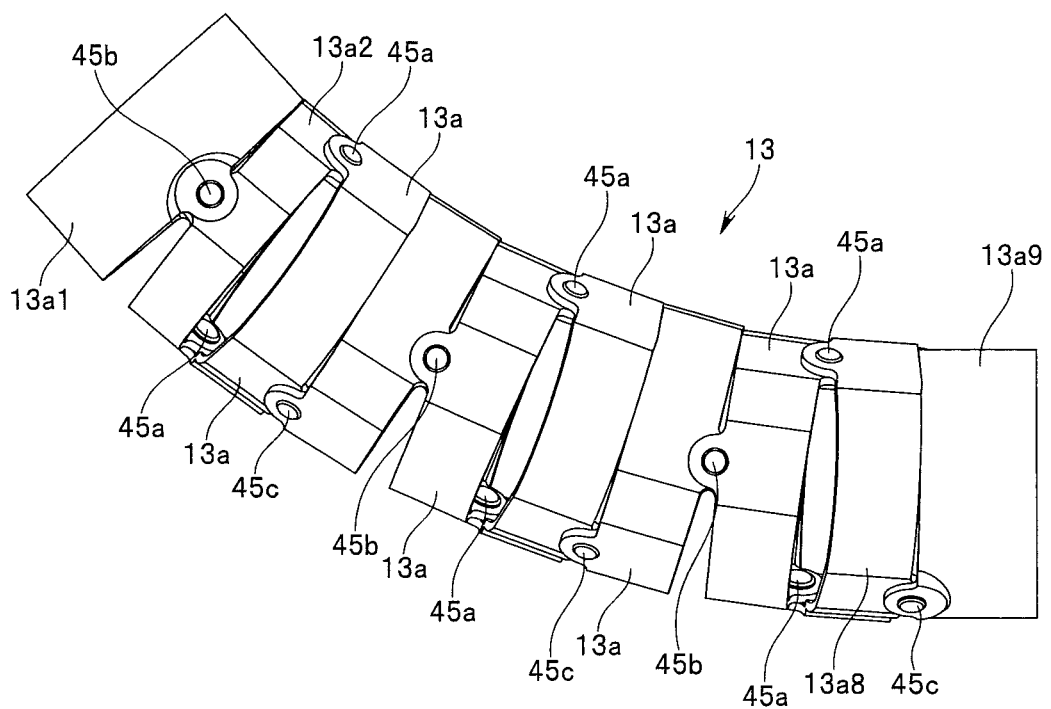
FIG. 8 is an enlarged perspective view illustrating the bending pieces constituting the passive bending portion in FIG. 7.

Furthermore, FIG. 6 is a diagram of the passive bending portion in FIG. 5 viewed from a direction VI in FIG. 5, FIG. 7 is a perspective view illustrating bending pieces constituting the active bending portion and bending pieces constituting the passive bending portion provided at the insertion portion of the endoscope in FIG. 1 before connection and FIG. 8 is an enlarged perspective view illustrating the bending pieces constituting the passive bending portion in FIG. 7.

Figure 9:
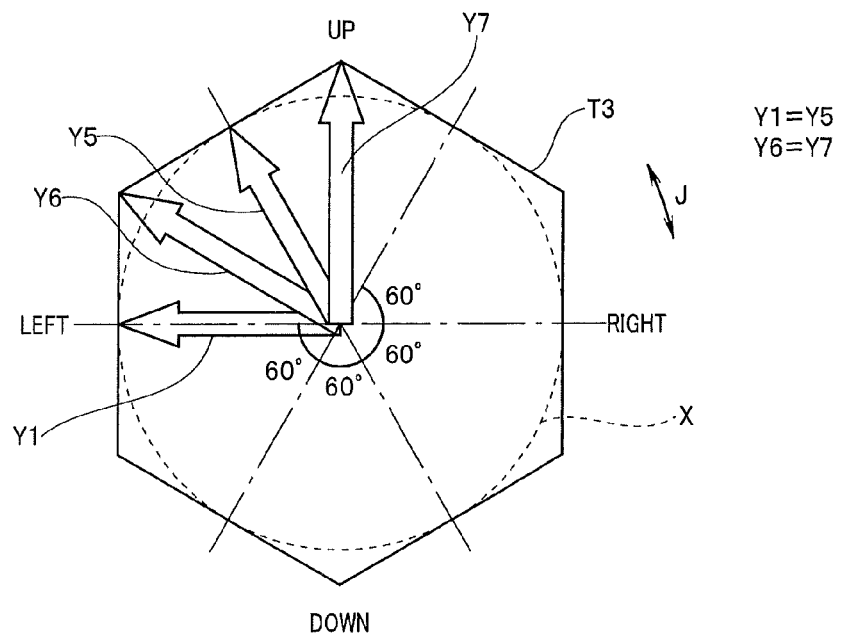
FIG. 9 is a diagram schematically illustrating a distribution of maximum bending angles in bending directions of the passive bending portion in FIG. 1 with three-axis bending capability.
Figure 10:
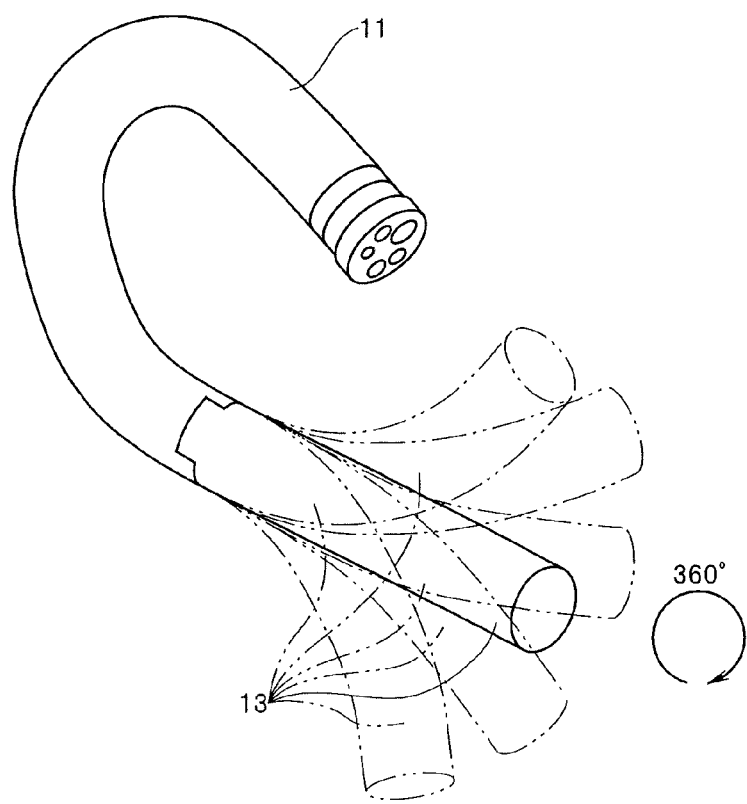
FIG. 10 is a perspective view schematically illustrating the passive bending portion provided at the insertion portion of the endoscope in FIG. 1 which is bent to a maximum angle in a plurality of directions.
Figure 11:
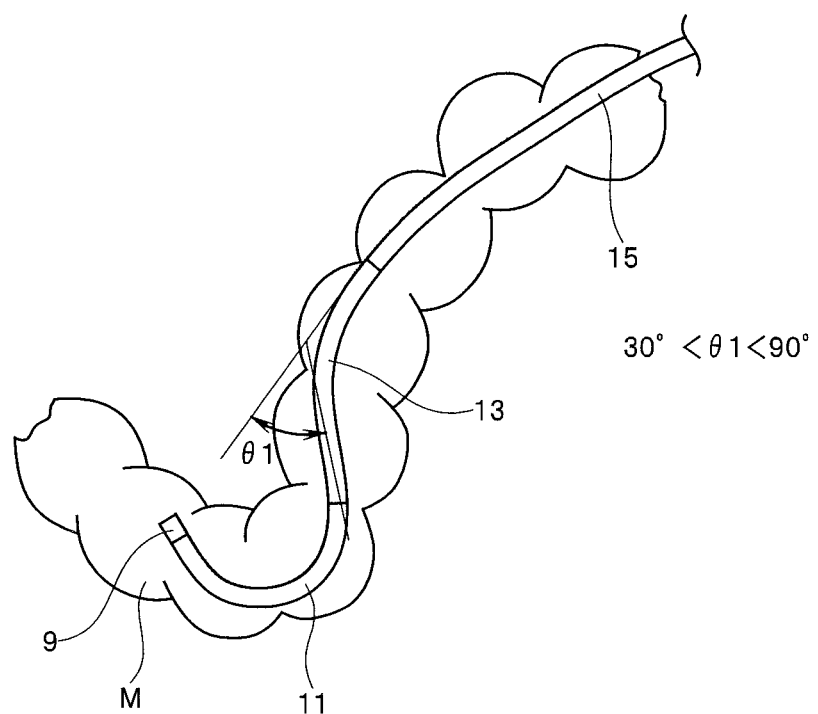
FIG. 11 is a perspective view schematically illustrating the active bending portion in FIG. 1 which is bent in the intestine with the maximum bending angle of the passive bending portion being more than 30° and less than 90°.

Furthermore, FIG. 9 is a diagram schematically illustrating a distribution of maximum bending angles in bending directions of the passive bending portion in FIG. 1 with three-axis bending capability, FIG. 10 is a perspective view schematically illustrating the passive bending portion provided at the insertion portion of the endoscope in FIG. 1 which is bent to a maximum angle in a plurality of directions and FIG. 11 is a perspective view schematically illustrating the active bending portion in FIG. 1 which is bent in the intestine with the maximum bending angle of the passive bending portion being more than 30° and less than 90°.

As shown in FIG. 1, principal parts of an endoscope system 1 are configured by including an insertion portion 5 inserted into a subject, an operation section 6 connected to the insertion portion 5 on the proximal end side, a universal cord 7 that extends from the operation section 6, and a connector 8 provided at an extending end of the universal cord 7. The endoscope 1 is electrically connected to an outside apparatus such as a control apparatus and an illumination apparatus via the connector 8.

The operation section 6 is provided with an upward/downward bending operation knob (hereinafter simply referred to as "knob") 3 and a leftward/rightward bending operation knob (hereinafter simply referred to as "knob") 4 that performs bending operation on an active bending portion 11 which will be described later.

The insertion portion 5 is constructed of a distal end portion 9, a bending portion 10 and a flexible tube section 15, and is formed in an elongated shape along an insertion direction W.

The distal end portion 9 includes an image pickup unit 20 shown in FIG. 2 used to observe the interior of a subject and an illumination unit (not shown) that illuminates the interior of the subject.

Furthermore, the bending portion 10 is constructed of the active bending portion 11 and a passive bending portion 13 provided on the proximal end side of the active bending portion 11.

The active bending portion 11 is bendable by 360° in four directions; upward, downward, leftward and rightward directions, or in directions combining the four directions; upward, downward, leftward and rightward directions according to a bending operation by an operator, accompanying the pulling or relaxing of bending wires 21 to 24 which will be described later (bending wires 23 and 24 are not shown in FIG. 3) inserted in the insertion portion 5 through the operation of the knob 3 or knob 4.

More specifically, as shown in FIG. 3, principal parts of the active bending portion 11 are constructed of a plurality of bending pieces 11a, a braid 31 that covers outer circumferences of the plurality of bending pieces 11a and coating resin 32 that coats an outer circumference of the braid 31.

The plurality of bending pieces 11a are pivotably connected in an insertion direction W as shown in FIG. 3 and FIG. 7, to be more specific, the bending pieces 11a adjacent to each other in the insertion direction W are pivotably connected together via a plurality of rivets 35a and 35b constituting rotation shafts located at positions differing by 90° in a circumferential direction J of the bending pieces 11a.

To be more specific, the bending pieces 11a adjacent to each other in the insertion direction W are connected pivotably in the upward and downward directions via the rivets 35a constituting two first opposed rotation shafts (only one shaft is shown in FIG. 3 and FIG. 7) and connected pivotably in the leftward and rightward directions via the rivets 35b constituting two second opposed rotation shafts at positions differing by 90° from the positions of the rivets 35a in the circumferential direction J.

As shown in FIG. 3 and FIG. 7, the adjacent bending pieces 11a are connected together via the rivets 35a and rivets 35b alternately, for example, the first bending piece 11a and the second bending piece 11a are connected together via the rivets 35a, the second bending piece 11a and the third bending piece 11a are connected together via the rivets 35b, the third bending piece 11a and the fourth bending piece 11a are connected together via the rivets 35a, . . . , and so forth.

Thus, the active bending portion 11 has a configuration bendable by 360° in four directions; upward, downward, leftward and rightward directions and in directions combining the four directions; upward, downward, leftward and rightward directions. That is, the active bending portion 11 has a configuration that performs the aforementioned two-axis bending in a plurality of directions.

As shown in FIG. 3, the four bending wires 21 to 24 (only bending wires 21 and 22 are shown in FIG. 3) are inserted in the active bending portion 11, located at positions differing by 90° in the circumferential direction J of the bending pieces 11a. The four bending wires 21 to 24 are located coaxially with the two rivets 35a and two rivets 35 respectively in the circumferential direction J.

Furthermore, the four bending wires 21 to 24 are supported by wire receivers 27 provided on the respective bending pieces 11a in the active bending portion 11 and the distal end of each wire 21 to 24 is connected to the bending piece 11a located at the outermost distal end in the insertion direction W among the plurality of bending pieces 11a. As a result, the active bending portion 11 performs two-axis bending as any one of the rivet 35a and rivet 35b rotates accompanying the pulling or relaxation of the bending wires 21 to 24.

The passive bending portion 13 cannot be bent according to a bending operation by the operator, but is passively bendable by 360° when an external force is applied thereto in four directions; upward, downward, leftward and rightward directions, or in directions combining the four directions; upward, downward, leftward and rightward directions. That is, the passive bending portion 13 has a configuration passively bendable without being actively bent by bending wires or other bending operation means.

More specifically, as shown in FIG. 5, principal parts of the passive bending portion 13 are constructed of a plurality of bending pieces 13a, a braid 131 that covers outer circumferences of the plurality of bending piece 13a, and coating resin 32 that coats an outer circumference of the braid 131.

The plurality of bending pieces 13a are pivotably connected in the insertion direction W as shown in FIG. 5 to FIG. 8, or to be more specific, the bending pieces 13a are pivotably connected via a plurality of rivets 45a to 45c constituting rotation shafts located at positions differing by 60° in the circumferential direction J of the bending pieces 13a.

To be more specific, as shown in FIG. 6, the bending pieces 13a adjacent to each other in the insertion direction W are connected pivotably in the insertion direction W via rivets 45a constituting two third opposed rotation shafts located coaxially with the rivets 35a of the active bending portion 11. Furthermore, the bending pieces 13a are pivotably connected via rivets 45b constituting two fourth opposed rotation shafts at positions 60° shifted from the rivets 45a in the circumferential direction J of the bending piece 13a. Furthermore, the bending pieces 13a are pivotably connected via rivets 45c constituting two fifth opposed rotation shafts at positions 60° shifted from the rivets 45a and the rivets 45b in the circumferential direction J of the bending piece 13a.

The bending pieces 13a adjacent to each other are connected via the rivets 45a, the rivets 45b and the rivets 45c alternately as shown in FIG. 5 and FIG. 7, for example, when the first bending piece 13a and the second bending piece 13a are connected together via the rivets 45a, the second bending piece 13a and the third bending piece 13a are connected together via the rivets 45b, further the third bending piece 13a and the fourth bending piece 13a are connected together via the rivets 45c and the fourth bending piece 13a and the fifth bending piece 13a are connected together via the rivets 45a, . . . , and so forth.

In this way, the passive bending portion 13 has a configuration bendable by 360° as shown in FIG. 10 in upward, downward, leftward and rightward directions and directions combining four directions; upward, downward, leftward and rightward directions. To be more specific, the passive bending portion 13 has a configuration in which all the rivets 45a to 45c are rotated when the passive bending portion 13 is bent in the upward and downward directions, and only the rivets 45b and 45c are rotated when the passive bending portion 13 is bent in the leftward and rightward directions.

Hereinafter, the bending according to the configuration in which the bending pieces 13a are connected together pivotably in the upward, downward, leftward and rightward directions via the plurality of rivets 45a to 45c located at positions differing by 60° in the circumferential direction J of the bending pieces 13a is called "three-axis bending."

Figure 18:
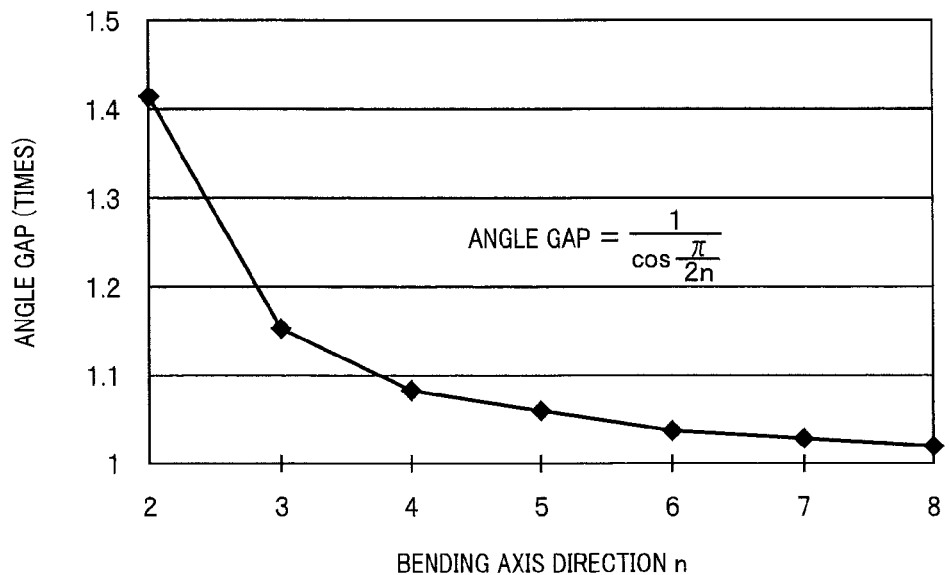
FIG. 18 is a diagram illustrating an angle gap with respect to the number of bending axes.
Figure 19:
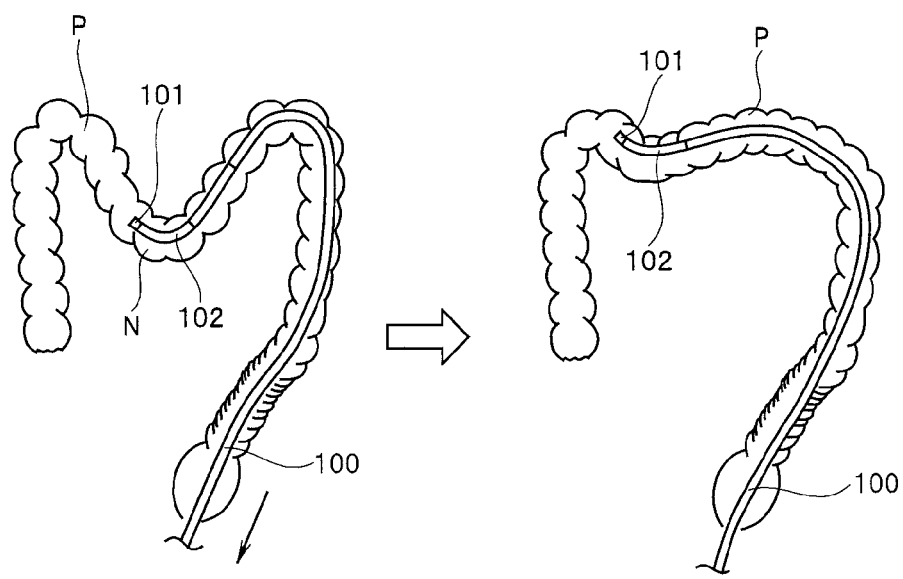
FIG. 19 is a diagram schematically illustrating an operation of raising the transverse colon using an endoscope having only an active bending portion.
Figure 20:
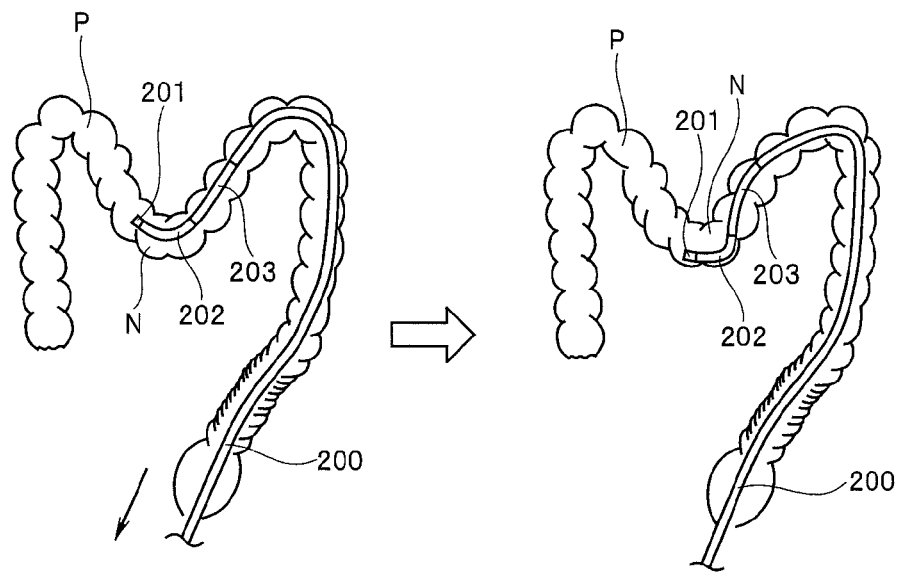
FIG. 20 is a diagram schematically illustrating an operation of raising the transverse colon using an endoscope having an active bending portion and a passive bending portion.
Figures 21A, 21B:
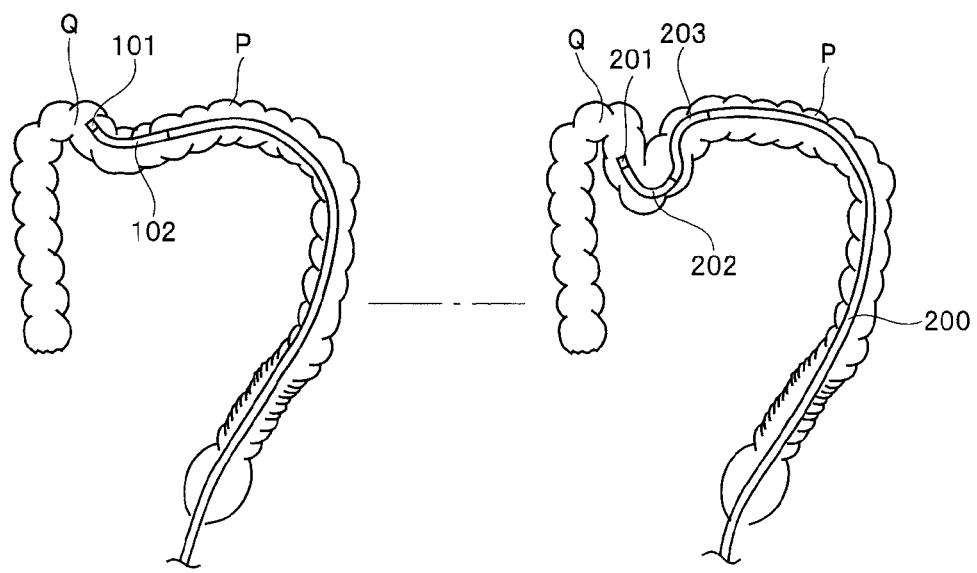
FIG. 21A is a diagram schematically illustrating an operation of causing the endoscope having only an active bending portion to pass through the hepatic flexure of the intestine.
FIG. 21B is a diagram schematically illustrating an operation of causing the endoscope having an active bending portion and a passive bending portion to pass through the hepatic flexure of the intestine.
Figure 22:
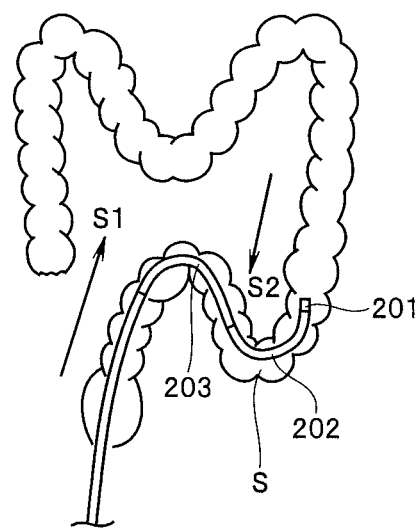
FIG. 22 is a diagram schematically illustrating an operation of causing the endoscope having an active bending portion and a passive bending portion to pass through the sigmoid colon of the intestine.

Furthermore, as shown in FIG. 9, when the passive bending portion 13 performs three-axis bending, of the aforementioned twist directions which are intermediate directions of upward, downward, leftward and rightward directions, a maximum bending angle Y5 shifted by 60° from the leftward and rightward directions in the circumferential direction J is equal to a maximum bending angle Y1 in the leftward and rightward directions (Y1=Y5), and a maximum bending angle Y6 in a twist direction except the direction shifted by 60° from the leftward and rightward directions in the circumferential direction J is geometrically known to be $1/\cos(\pi/6) \approx 1.15$ times the maximum bending angles Y1 in the leftward and rightward directions and Y5 in the direction shifted by 60° from the leftward and rightward directions in the circumferential direction J as shown in aforementioned FIG. 18 (Y6=1.15Y1 (Y5)).

That is, the angle gap resulting from the difference in maximum bending angles of the maximum bending angle Y6 is 1.15 times compared to that of the maximum bending angle Y1 or Y5. This angle gap is 1.41 times that in the case of two-axis bending as shown in FIG. 16 and FIG. 18 as described above and 1.08 times in the case of four-axis bending as shown in FIG. 16 and FIG. 17 as described above, and therefore it is known that the change in the angle gap from the two-axis bending to three-axis bending (1.41−1.15=0.26) is much greater than the change from the three-axis bending to four-axis bending (1.15−1.08=0.07).

As described above, the maximum bending angle preferably remains to be the same whether the passive bending portion 13 is bent in the upward and downward directions, bent in the leftward and rightward directions, that is, bent in any direction of 360°. That is, the maximum bending angle shown in FIG. 9 preferably becomes the track of a circle X shown by a dotted line.

Figure 16:
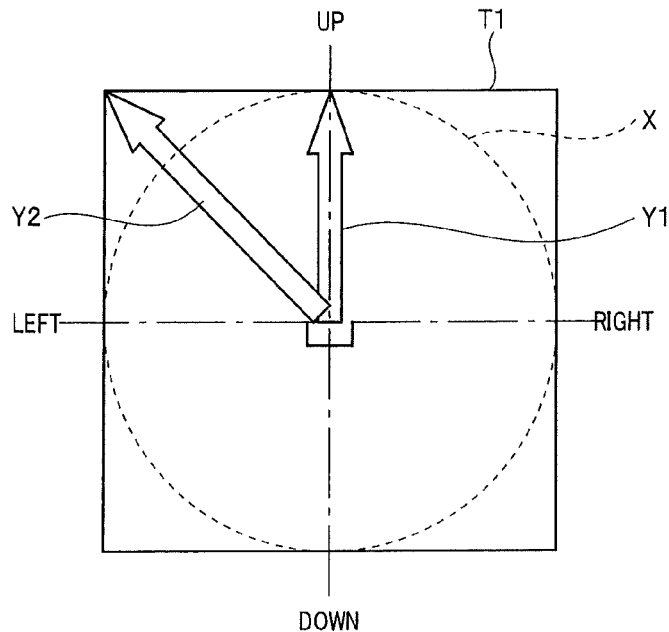
FIG. 16 is a diagram schematically illustrating a distribution of maximum bending angles in bending directions of the bending portion with two-axis bending capability.
Figure 17:
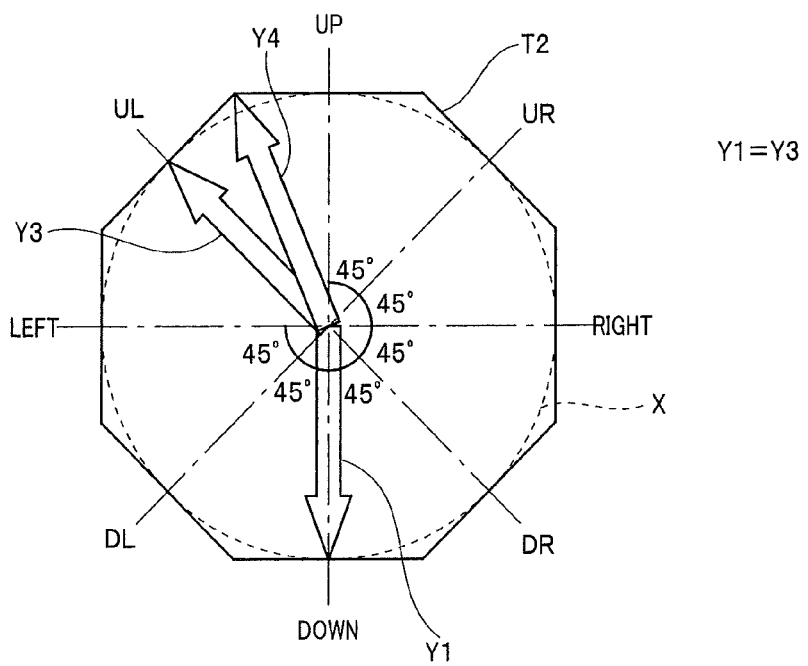
FIG. 17 is a diagram schematically illustrating a distribution of maximum bending angles in bending directions of the bending portion with four-axis bending capability.

Thus, since the actual track of maximum bending angle of the passive bending portion 13 of the present embodiment becomes a hexagonal shape shown by a solid line T3 shown in FIG. 9, which approximates to the circle X, it is thereby possible to significantly reduce the difference in maximum bending angles by the bending direction compared to the aforementioned two-axis bending shown in FIG. 16, although it is slightly greater than the aforementioned four-axis bending shown in FIG. 17.

That is, as shown in FIG. 10, the passive bending portion 13 is configured so that the maximum bending angle remains substantially constant even when the passive bending portion 13 is changed from an unbent state to a maximum-bent state in any direction of 360°.

Furthermore, if the length of the passive bending portion 13 in the insertion direction W is assumed to be constant, since the three-axis bending requires three bending pieces while the two-axis bending requires two bending pieces to bend in the upward, downward, leftward and rightward directions, the bending piece 13a with three-axis bending capability becomes shorter in the insertion direction W, whereas since the four-axis bending requires four bending pieces, the bending piece 13a with three-axis bending capability becomes longer in the insertion direction W than the bending pieces with four-axis bending capability, and can thereby maintain strength more than the bending pieces used for four-axis bending.

Here, in the present embodiment, as shown in FIG. 9, the direction in which the bending angle of the passive bending portion becomes a maximum angle, to be more specific, the direction shown by the arrow Y6 in which the bending angle becomes 1.15 times the other bending angles is defined to match the upward/downward direction (Y6=Y7). This is because since bending operation in upward and downward directions is the operation mainly used in the endoscope, the passive bending portion may be preferably bent in the upward and downward directions more than in the leftward and rightward directions or other directions.

The relationship regarding maximum bending angles in different bending directions have been described so far, but this relationship is also applicable to the radius of curvature. To be more specific, assuming that of maximum bending angles, a maximum bending angle in the bending direction which is a minimum angle is θ3, and a maximum bending angle in the bending direction which is a maximum angle is θ4, their relationship is defined as θ4=α×θ3.

Here, as described above, α is 1.41 in the case of two-axis bending, 1.15 in the case of three-axis bending and 1.08 in the case of four-axis bending. Furthermore, assuming that the radius of curvature in the case of θ3 is r3 and the radius of curvature in the case of θ4 is r4, since the length of the bending pieces constituting the bending tube is unchanged and the lengths of the respective arcs are unchanged, it is possible to define 2×r3×θ3=2×r4×θ4.

Thus, since r4=r3×θ3/θ4=r3×θ3/(α×θ3), that is, (1/α)×r3, it is clear that the radius of curvature becomes a reciprocal multiple of the angle gap.

Furthermore, since the passive bending portion 13 has the aforementioned three-axis bending configuration and the number of bending pieces 13a, interval between the bending pieces 13a in the insertion direction W and angle θ2 between the bending pieces shown in FIG. 5 are set to predetermined values, the maximum bending angle is set to be more than 30° and less than 90° as shown in FIG. 11.

As is generally known, the bending angle of the passive bending portion 13 is defined by the bending pieces 13a adjacent in the insertion direction W coming into contact with each other as the rivets 45a to 45c rotate in the plurality of bending pieces 13a as shown in FIG. 8.

If the difference in maximum bending angles by the bending direction is reduced, a three-axis bending configuration may also be applied to the active bending portion 11. However, in the case of three-axis bending as described above, since it has a configuration in which all the rivets 45a to 45c are rotated when the active bending portion is bent in the upward and downward directions and only the rivets 45b and 45c are rotated when the active bending portion is bent in the leftward and rightward directions, and moreover, when the three-axis bending configuration is applied to the active bending portion 11, the two of the bending wires 21 to 24 are coaxial with the rivet 45a in the circumferential direction J, but the remaining two wires are shifted in the circumferential direction J with respect to the rivets 45b and 45c.

For this reason, when three-axis bending is performed, any one of the bending wires 21 to 24 is pulled and if the rivets 45b and 45c located at positions differing from the bending wires in the circumferential direction J rotate in different directions, the bending pieces 11a adjacent to each other in the insertion direction W rotate in different directions. For this reason, since the bending wires are supported by the wire receivers 27 of the bending pieces 11a constituting the active bending portion 11, the bending wires cannot maintain the rectilinear shape but become zigzag-shaped because the adjacent bending pieces 11a rotate in different directions. As a result, sufficient pulling force cannot be given from the bending wires to the active bending portion 11. Therefore, the present embodiment adopts a two-axis bending configuration for the active bending portion 11.

Returning to FIG. 5, the outer circumferences of the aforementioned four bending wires 21 to 24 inserted in the plurality of bending pieces 13a of the passive bending portion 13 are covered with known coil pipes 91 to 94 (coil pipes 93 and 94 are not shown in FIG. 5) and the coil pipes 91 to 94 are fixed to a pipe sleeve 40 by welding or the like.

Furthermore, as shown in FIG. 8, of the plurality of bending pieces 13a of the passive bending portion 13, the rivet 45b on a bending piece 13a1 located on the outermost distal end side is set in a hole formed in a pivoted section protruding in a semicircular shape on the proximal end side, and the rivet 45b on a bending piece 13a2 located as the second from the distal end, is set in a hole formed in a pivoted section protruding in a semicircular shape on the distal end side, both pivoted sections are superimposed one on the other so that the holes overlap, and the bending piece 13a1 and the bending piece 13a2 are then pivotably connected via the rivets 45b set in the respective holes, and in this case, both pivoted sections are superimposed in such a way that the pivoted section of the bending piece 13a2 is located more inside than the pivoted section of the bending piece 13a1 in the diameter direction.

This is because, if on the contrary, the pivoted sections are superimposed in such a way that the pivoted section of the bending piece 13a2 is located outside with respect to the pivoted section of the bending piece 13a1 in the diameter direction, a configuration is normally used in which the pivoted section of the bending piece 13a1 is provided with a semicircular concave section and the pivoted section protruding in a semicircular shape of the bending piece 13a2 is set in the pivoted section to prevent the outside shape of the bending piece 13a1 from growing. However, since the distal end of the aforementioned braid 131 is fixed to the bending piece 13a1 by solder or the like, if the concave section is formed in the bending piece 13a1, solder flows into the concave section when the distal end of the braid 131 is fixed and the rotation of the rivet 45b is fixed by the solder flowing over the bottom surface of the concave section. This problem can be solved by increasing the soldered area in the bending piece 13a1 along the insertion direction W, but in this case, the connection range between the passive bending portion 13 and the active bending portion 11 extends along the insertion direction W, which is not desirable.

Furthermore, as shown in FIG. 8, even when the pivoted sections are superimposed so that the pivoted section of the bending piece 13a2 is located more inside in diameter direction than the pivoted section of the bending piece 13a1, if solder flows into the rivet 45b, the rotation of the rivet 45b is naturally fixed.

However, in the configuration shown in FIG. 8, the distance from the distal end of the braid 131 to the rivet 45b in the insertion direction W is longer by the radius of the concave section than the distance from the distal end of the braid 131 to the semicircular concave section formed in the bending piece 13a1 in the insertion direction W in the aforementioned configuration in which the pivoted sections are superimposed in such a way that the pivoted section of the bending piece 13a2 is located outside in diameter direction with respect to the pivoted section of the bending piece 13a1, and therefore solder is less likely to flow into the rivet 45b.

The same also applies to the rear end side of the passive bending portion 13, and also when the pivoted section that protrudes in a semicircular shape of the bending piece 13a8 located second closest to the proximal end side is superimposed on the pivoted section that protrudes in a semicircular shape of the bending piece 13a9 located closest to the proximal end side out of the plurality of bending pieces 13a, the pivoted sections are superimposed one on the other so that the pivoted section of the bending piece 13a8 is located more inside than the pivoted section of the bending piece 13a9 in the diameter direction.

Furthermore, the active bending portion 11 and the passive bending portion 13 having the above-described configurations are connected together via a pipe sleeve 40 with the outer circumferences of the bending pieces 11a and 13a which are not coated with the coating resin 32 being covered with the braids 31 and 131 as shown in FIG. 4 and FIG. 7.

To be more specific, as shown in FIG. 7, a concave section 11h is formed on the outer circumference on the proximal end side of a bending piece 11af located closest to the proximal end side out of the plurality of bending pieces 11a, and a convex section 13t that engages with the concave section 11h is formed on the outer circumference on the distal end side of a bending piece 13a1 located closest to the distal end side out of the plurality of bending pieces 13a, and the bending pieces 11af and 13a1 are fixed to the pipe sleeve 40 via a screw or the like with the convex section 13t being engaged with the concave section 11h.

This is simply intended to allow the connection length in the insertion direction W between the active bending portion 11 and the passive bending portion 13 to be shorter than that in the structure in which the bending pieces 11af and 13a1 are fixed to the pipe sleeve 40 with the outer circumference end face on the rear end side of the bending piece 11af being simply placed opposed to the outer circumference end face on the distal end side of the bending piece 13a1.

Furthermore, the concave and convex sections used for connection between the active bending portion 11 and the passive bending portion 13 are not covered with the braids 31 and 131. That is, the braid 31 is fixed closer to the distal end side than the concave section 11h by solder or the like and the braid 131 is fixed closer to the rear end side than the convex section 13t by solder or the like. Therefore, the braids 31 and 131 are not bonded to the concave and convex sections.

This is because, during the formation of the active bending portion 11, if a concave section is formed at the rear end of the bending piece 11af, when covering the outer circumference of the bending piece 11a with the braid 31 and fixing the braid 31, it is necessary to remove the braid only from the part dented on the distal end side of the concave section, and such a removing operation is difficult.

The same also applies to the passive bending portion 13, and during the formation of the passive bending portion 13, if a convex section is formed at the distal end of the bending piece 13a1, when covering the outer circumference of the bending piece 13a with the braid 131, it is necessary to remove the braid on both sides of the part of the convex section protruding on the distal end side, and such a removing operation is difficult.

That is, if the braids 31 and 131 are bonded and fixed to the concave section 11h and the convex section 13t, when removing the braids from the concave and convex sections, it is necessary to cut the braid according to the concave and convex shapes, and such a cutting operation is difficult. However, if the braids 31 and 131 are not bonded to the concave section 11h and the convex section 13t, when removing the braids from the concave and convex sections, it is possible to cut the respective braids into a circular shape while ignoring the concave and convex shapes, and such a cutting operation is quite easy.

Thus, the outer circumference of the pipe sleeve 40 is not covered with the braids 31 and 131 as shown in FIG. 4. This configuration also contributes to the effect of preventing the outside diameter from increasing by bonding allowance of the braids 31 and 131 in the joining portion between the active bending portion 11 and the passive bending portion 13 in the pipe sleeve 40.

Furthermore, as shown in FIG. 4, the inner diameter c of the passive bending portion 13 is set to be equal to or above the inner diameter a of the active bending portion 11 and the inner diameter a of the active bending portion 11 is set to be equal to or above the inner diameter b of the pipe sleeve 40 (b<ac).

This is because since coil pipes 91 to 94 inserted in the passive bending portion 13 are thicker than the bending wires 21 to 24, the coil pipes 91 to 94 are more likely to interference with the rivets 45a to 45c, and therefore if the inner diameter c of the passive bending portion 13 is formed to be greater than the inner diameter b of the pipe sleeve 40 and equal to or above the inner diameter a of the active bending portion 11, since the coil pipes 91 to 94 are located inside in the diameter direction with respect to the rivets 45a to 45c, it is possible to prevent interference with respect to the rivets 45a to 45c from the coil pipes 91 to 94.

This is for the same reason that the inner diameter of the active bending portion a is formed to be greater than the inner diameter b of the pipe sleeve 40, and by arranging the bending wires 21 to 24 more inside than the rivets 35a and 35b in the diameter direction, it is possible to prevent interference with respect to the rivets 35a and 35b from the bending wires 21 to 24.

Furthermore, the active bending portion 11 and the passive bending portion 13 may also be formed into a single continuous bending portion without using the pipe sleeve 40.

Thus, the present embodiment has described the passive bending portion 13 as having a three-axis bending configuration bendable by 360° in upward, downward, leftward and rightward directions and in directions combining the four directions; upward, downward, leftward and rightward directions.

In this way, though the difference in maximum bending angles by the bending direction is slightly greater than the aforementioned four-axis bending shown in FIG. 17, the difference becomes by far smaller than the aforementioned two-axis bending shown in FIG. 16.

Furthermore, assuming the length of the passive bending portion 13 in the insertion direction W is constant, the bending pieces 13a with three-axis bending capability are shorter than the bending pieces with two-axis bending capability in the insertion direction W, but since they are longer than the bending pieces with four-axis bending capability in the insertion direction W, they can maintain strength more than the bending pieces used for four-axis bending.

Furthermore, the number of rivets connecting the bending pieces 13a with three-axis bending capability and the number of bending pieces are greater than the number of rivets connecting the bending pieces with two-axis bending capability and the number of bending pieces, but these are smaller than the number of rivets connecting the bending pieces with four-axis bending capability and the number of bending pieces, and it is thereby possible to reduce the manufacturing cost to a minimum.

That is, it is apparent that applying the three-axis bending configuration to the passive bending portion 13 is most suitable when a variation in maximum bending angles, manufacturing cost and strength of the bending pieces are taken into consideration.

As described above, it is possible to minimize the difference in maximum bending angles by the bending direction of the passive bending portion while reducing the manufacturing cost and suppressing deterioration of strength of the bending piece 13a to a minimum.

Furthermore, since the difference in maximum bending angles by the bending direction of the passive bending portion 13 is reduced, it is possible to prevent the aforementioned rotation of an endoscope image resulting from excessive bending of the passive bending portion 13 in twist directions.

Furthermore, the present embodiment has shown that the passive bending portion 13 has the aforementioned three-axis bending configuration and the number of bending pieces 13a, interval between the bending pieces 13a in the insertion direction W and angle θ2 between the bending pieces shown in FIG. 5 are set to predetermined values so that the maximum bending angle is set to be more than 30° and less than 90° as shown in FIG. 11.

Hereinafter, the effects thereof will be described using FIG. 12 and FIG. 13.

Figure 12A:
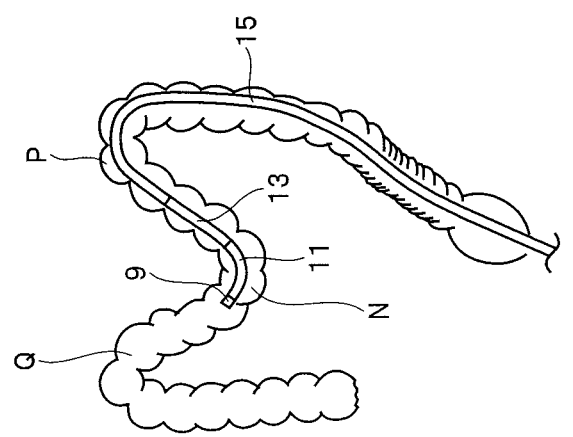
FIG. 12A is a diagram schematically illustrating the distal end portion of the insertion portion of the endoscope in FIG. 1 with the active bending portion being bent and made to pass through a descending portion of the transverse colon of the large intestine.
Figure 12B:
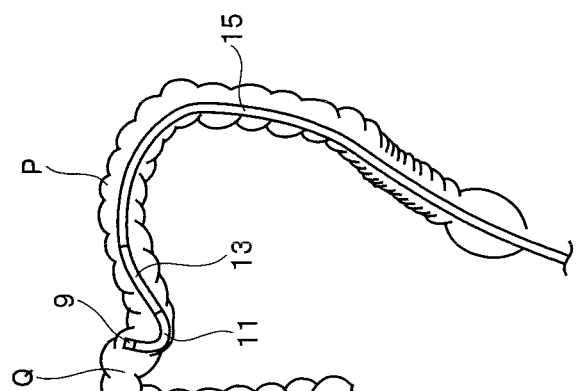
FIG. 12B is a diagram schematically illustrating an operation of raising the descending portion and straightening the transverse colon by pulling the insertion portion toward the proximal end side with the distal end portion which has passed through the descending portion in FIG. 12A being hooked thereat.
Figure 12C:
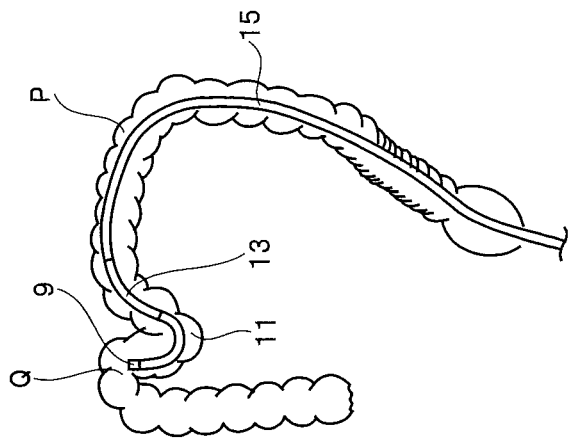
FIG. 12C is a diagram schematically illustrating an operation of entering the distal end of the endoscope into the hepatic flexure with the transverse colon being straightened.

FIG. 12A is a diagram schematically illustrating the distal end portion of the insertion portion of the endoscope in FIG. 1 with the active bending portion being bent and made to pass through a descending portion of the transverse colon of the large intestine, FIG. 12B is a diagram schematically illustrating an operation of raising the descending portion and straightening the transverse colon by pulling the insertion portion toward the proximal end side with the distal end portion which has passed through the descending portion in FIG. 12A being hooked thereat and FIG. 12C is a diagram schematically illustrating an operation of entering the distal end of the endoscope into the hepatic flexure with the transverse colon being straightened.

FIG. 13A is a diagram illustrating the distal end portion of the insertion portion of the endoscope in FIG. 1 with the active bending portion being bent and made to enter into the flexural area, FIG. 13B is a diagram schematically illustrating the insertion portion in FIG. 13A pushed in so as to press the active bending portion and the passive bending portion against the flexural area, FIG. 13C is a diagram schematically illustrating the active bending portion which has passed through the flexural area along the wall surface of the flexural area, FIG. 13D is a diagram schematically illustrating an intermediate state of the passive bending portion passing through the flexural area along the wall surface of the flexural area and FIG. 13E is a diagram schematically illustrating the passive bending portion which has passed through the flexural area along the wall surface of the flexural area.

If the maximum bending angle of the passive bending portion 13 is set to be more than 30° and less than 90°, when, as shown in FIG. 12A, the insertion portion 5 is inserted into the transverse colon P of the large intestine, the active bending portion 11 is bent, the distal end portion 9 thereof is made to pass through the descending portion N of the transverse colon P and the insertion portion 5 is pulled back to straighten the transverse colon with the distal end portion 9 being hooked at the transverse colon P, it is possible to prevent the distal end portion 9 from being twisted as a result of the passive bending portion 13 being bent excessively. For this reason, as shown in FIG. 12B, the distal end portion 9 is not likely to be unhooked from the transverse colon P.

Thus, the transverse colon P can be reliably straightened. Furthermore, as shown in FIG. 12C, since the distal end portion 9 can be reliably entered into the flexural area of the hepatic flexure Q, even when the passive bending portion 13 is provided, it is possible to secure operability comparable to that of an endoscope provided with only an active bending portion.

Furthermore, as shown in FIG. 13A, when the insertion portion 5 of the endoscope 1 is made to pass through a flexural area G, the distal end portion 9 is first made to pass up to a point past the flexural area G with the active bending portion 11 being bent upward and the insertion portion is further pushed in, the passive bending portion 13 is pressed against the intestinal wall as the insertion portion 5 is pushed in as shown in FIG. 13B, and the passive bending portion 13 is thereby bent upward to a maximum angle as in the case of the active bending portion 11.

In this case, as described above, since the difference in maximum bending angles between the upward direction and the twist direction is reduced in the passive bending portion 13, it is possible to prevent an endoscope image captured by the image pickup unit 20 provided in the insertion portion 5 from rotating.

Furthermore, if the passive bending portion 13 is bent at a small radius of curvature, the excessively bent passive bending portion 13 knocks up the wall surface of the flexural area G, resulting in a problem with a known knocking-up phenomenon, but since the maximum bending angle of the passive bending portion 13 is set to be more than 30° and less than 90°, it is possible to allow the active bending portion 11 and the passive bending portion 13 to smoothly pass along the wall surface of the flexural area G as shown in FIG. 13C and FIG. 13D. This is because since the difference in the radius of curvature by the insertion direction is reduced, a knocking-up phenomenon is less likely to occur.

The lower limit value of the maximum bending angle of the passive bending portion 13 is set to 30° because an excessively small degree of bending of the passive bending portion 13 also prevents passage through the flexural area G and the passage through the flexural area G of 180° as shown in FIG. 13A to FIG. 13E, for example, requires a bending greater than a minimum of 30°.

As described above, it is possible to provide the endoscope 1 having a configuration that minimizes the difference in maximum bending angles by the bending direction in the passive bending portion 13 while reducing the manufacturing cost and suppressing deterioration of the strength of the bending pieces 13a, and can prevent the passive bending portion 13 from excessively bending depending on the bending direction and prevent the radius of curvature from decreasing.

Figure 14:
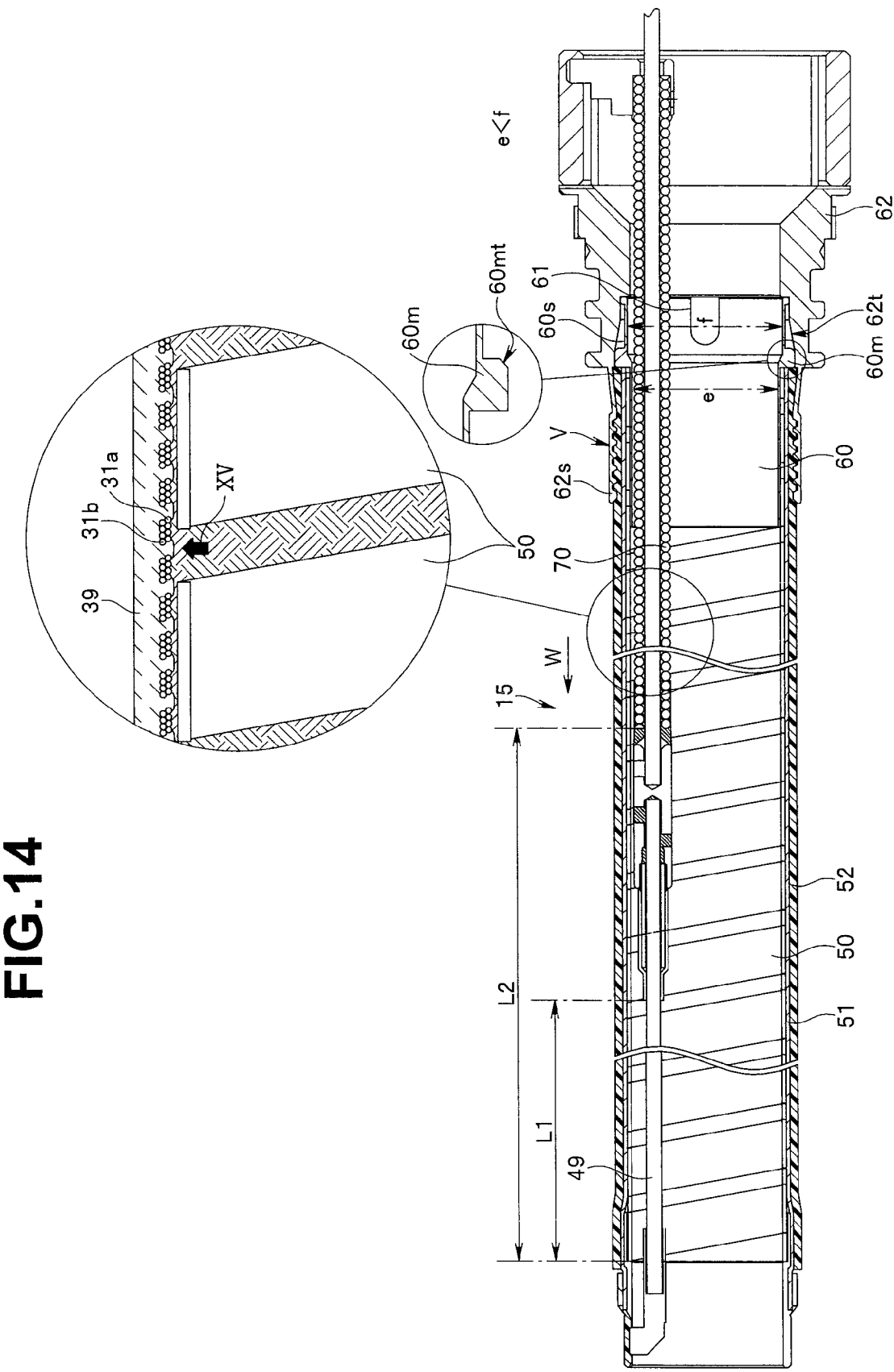
FIG. 14 is a partial cross-sectional view schematically illustrating a configuration of a flexible tube section of the insertion portion of the endoscope in FIG. 1.

FIG. 14 is a partial cross-sectional view schematically illustrating a configuration of a flexible tube section of the insertion portion of the endoscope in FIG. 1.

As shown in FIG. 14, the flexible tube section 15 is normally configured such that the outer circumference of an elongated flex 50 is covered with a braid 51 along the insertion direction W and the outer circumference of the braid 51 is coated with coating resin 52. The flex 50 is formed, spirally wound with a ribbon-like plate.

Furthermore, a configuration of the flexible tube section 15 is also known in which, for example, the hardness of the coating resin is made to increase from the distal end to the proximal end for the purpose of improving insertability of the insertion portion 5. That is, the distal end side of the flexible tube section 15 connected to the proximal end of the passive bending portion 13 is formed to be soft.

Thus, if the length of the soft region on the distal end side of the flexible tube section 15 (hereinafter referred to as "first flexible portion") in the insertion direction W is insufficient, the rigid region of the flexible tube section 15 enters the flexural area before the connection section between the passive bending portion 13 and the flexible tube section 15 completes passing through the flexural area, which may prevent the insertion portion from passing through the flexural area.

Therefore, in the present configuration, as shown in FIG. 14, a length L1 of the first flexible portion in the insertion direction W is set to be equal to or above a radius of curvature $R \times \pi/2$ corresponding to maximum bending in the vicinity of the rear end of the passive bending portion 13. That is, when the maximum bending angle of the passive bending portion 13 is set to be less than 90°, the length of L1 is set to be equal to or above the length when the passive bending portion 13 is bent by 90°.

Thus, since the sufficient length L1 of the first flexible portion in the insertion direction W can be secured, passage of the insertion portion 5 through the flexural area is never blocked.

Furthermore, as shown in FIG. 14, in the present configuration, a second flexible portion which is harder than the first flexible portion and softer than the rigid portion is formed between the first flexible portion and the rigid portion. To be more specific, the second flexible portion is formed between the proximal end of the first flexible portion and the distal end of a coil 70 in a known hardness variable mechanism 49 that makes variable the hardness of the flexible tube section 15 in the rigid portion inserted in the flexible tube section 15.

The length L2 of the second flexible portion in the insertion direction W is also set to be equal to or above the radius of curvature of $R \times \pi/2$ corresponding to maximum bending in the vicinity of the rear end of the passive bending portion 13.

In this way, it is possible to secure the sufficient length L2 of the second flexible portion in the insertion direction W, that is, secure a sufficient range in which the hardness is not variable by the hardness variable mechanism 49 on the distal end side of the flexible tube section 15, thus preventing passage of the insertion portion 5 through the flexural area from being blocked.

Furthermore, in the present configuration, the distal end of the hardness variable mechanism 49 is fixed to the joining section between the passive bending portion 13 and the flexible tube section 15 as shown in FIG. 5 and FIG. 14.

This is because since the passive bending portion 13 is soft, if the distal end of the hardness variable mechanism 49 is fixed to the joining section between the active bending portion 11 and the passive bending portion 13, the passive bending portion 13 may be unintentionally bent as the hardness variable mechanism 49 extends or contracts.

However, if the distal end of the hardness variable mechanism 49 is fixed in a manner movable in the insertion direction W, it is possible to prevent the passive bending portion 13 from being unintentionally bent, and therefore the distal end of the hardness variable mechanism 49 may be fixed to the pipe sleeve 40.

Figure 15:
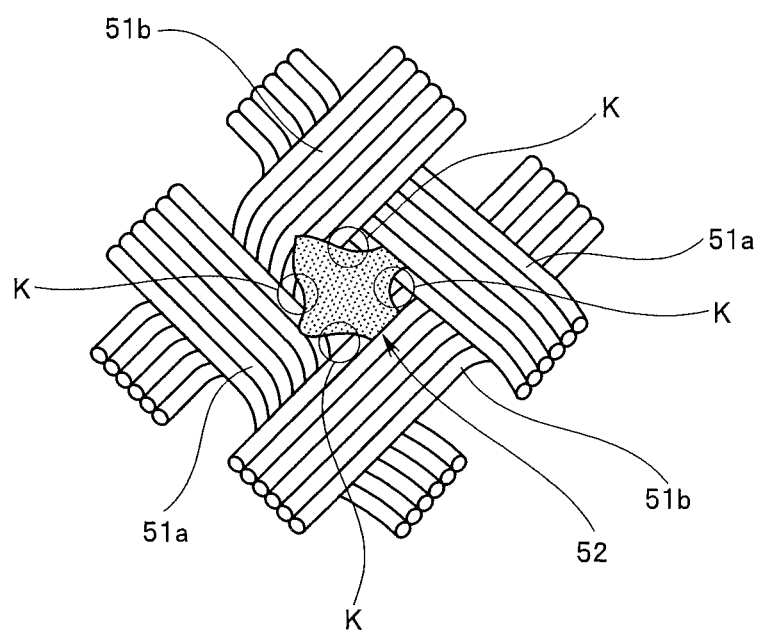
FIG. 15 is a partial perspective view of braids and coating resin of the flexible tube section in FIG. 14 viewed from a direction XV in FIG. 14.

FIG. 15 is a partial perspective view of the braid and coating resin of the flexible tube section in FIG. 14 viewed from a direction XV in FIG. 14.

The flex 50, the braid 51 and the coating resin 52 constituting the flexible tube section 15 have excellent flexibility, and they are generally formed into a single piece by causing the coating resin 52 to permeate into the flex 50 and the braid 51 to improve durability.

However, if the flex 50, the braid 51 and the coating resin 52 are integrated into one unit, the movement of each element is blocked, resulting in a problem that transmissibility of the force of pushing in the flexible tube section 15 deteriorates.

Thus, as shown in FIG. 14 and FIG. 15, the present configuration provides the braid 51 which is made up of a plurality of wire bundles 51a wound in one direction and a plurality of wire bundle 51b wound in another direction opposite to the one direction, the wire bundles in different winding directions being braided so as to sequentially change their inside-outside relationship and further braiding being performed such that one wire bundle coming out from the inside crosses two or more wire bundles of different winding directions until it goes into the inside again, in which, through optimization of its core member and fusion condition, the coating resin 52 in a fused state enters the gaps between the wire bundles of the braid 51 such that it does not enter the inside of the outer circumferential face of the flex 50 and the resin 52 that has entered extends over the inner surface of the braid 51 so as to cross at least one or more wire bundles and the extension of the resin 52 is outside the area in which the wire bundles 51a and 51b cross each other. That is, in this configuration, the resin 52 is not bonded in intersections K between the wire bundle 51a and the wire bundle 51b on the inner surface of the braid 51.

According to such a configuration, the wire bundle 51a and the wire bundle 51b are not completely fixed via resin 52 and the flex 50 is not fixed via the resin 52 either, and therefore the wire bundles 51a and 51b can easily move, thus making it possible to improve transmissibility of the force of pushing in the flexible tube section 15.

Here, a configuration is known in which the proximal end portion of the flexible tube section 15 is fixed to the distal end side of the operation section with the flex 50, the braid 51 and the coating resin 52 sandwiched between an inside pipe sleeve provided inside the proximal end portion of the flexible tube section 15 and an outside pipe sleeve provided on the distal end side of the operation section to which the proximal end portion of the flexible tube section is connected.

However, since the outside pipe sleeve only contacts the coating resin in this configuration, there are problems that it is not possible to establish electric conduction between the outside pipe sleeve, the flex 50 and the braid 51 and it is not possible to allow static electricity in the flexible tube section 15 to escape, and when the endoscope is used together with a high frequency treatment instrument, a high frequency current in the flexible tube section 15 is not allowed to escape.

Thus, as shown in FIG. 14, in the present configuration as in the case of the conventional art, the flex 50, the braid 51 and the coating resin 52 are sandwiched in a swage V between a distal end side region 62s of an outside pipe sleeve 62 and an inside pipe sleeve 60, the proximal end side of the flexible tube section 15 is thereby fixed and the outside pipe sleeve 62 and the inside pipe sleeve 60 are electrically connected in an area other than the swage V.

To be more specific, a configuration for electrically contacting the outside pipe sleeve 62 and the inside pipe sleeve 60 is provided in which a spring engagement section 60s is provided which is deformable because a plurality of slits 61 are formed in the insertion direction W on the rear end side of the inside pipe sleeve 60, an outside diameter of which is formed to be greater than the inner diameter of the outside pipe sleeve 62, and when the spring engagement section 60s is set in the region behind the distal end portion 62s of the outside pipe sleeve 62, the spring engagement section 60s that expands outward in the diameter direction is contracted in diameter by the outside pipe sleeve 62.

Furthermore, since an inner diameter f of the spring engagement section 60s is set to be greater than an inner diameter e of the region of the other inside pipe sleeve 60 (e<f), even when the spring engagement section 60s is contracted in diameter by the outside pipe sleeve 62, the diameter of the spring engagement section 60s is configured not to become smaller than a minimum inner diameter of the flexible tube section 15.

Furthermore, a tapered surface 62t is formed on the inner surface of the region in which the spring engagement section 60s of the outside pipe sleeve 62 is set so that the diameter of the inner surface of the outside pipe sleeve 62 decreases from the distal end side to the proximal end side.

Furthermore, a flange section 60m is formed on the outer circumference on the distal end side of the spring engagement section 60s and a chamfer section 60mt is also formed at the corner on the proximal end side that contacts the tapered surface of the flange section 60m.

As described so far, the spring engagement section 60s is smoothly set in the outside pipe sleeve 62 by means of the chamfer section 60mt and the tapered surface 62t, and the flange section 60m and the spring engagement section 60s of the inside pipe sleeve reliably contact the outside pipe sleeve 62, and it is thereby possible to reliably establish electric conduction of the flex 50 and the braid 51 with the outside pipe sleeve 62.

What is claimed is:

1. An endoscope comprising:
an insertion portion inserted into a subject;
an active bending portion provided in the insertion portion and bendable according to a bending operation of an operator, the active bending portion comprising a plurality of bending pieces arranged adjacently to each other in an insertion direction of the insertion portion which are pivotably connected to each other by a plurality of rotation shafts, the rotation shafts being located at positions differing from each other by 90° in a circumferential direction of the bending pieces; and
a passive bending portion provided closer to a proximal end side in the insertion direction than the active bending portion in the insertion portion and not bendable according to a bending operation of the operator but passively bendable when an external force is applied to the passive bending portion, the passive bending portion comprising a plurality of bending pieces arranged adjacently to each other in the insertion direction which are pivotably connected to each other by a plurality of rotation shafts, the rotation shafts being located at positions differing from each other by 60° in the circumferential direction,
wherein the active bending portion has a configuration in which the bending pieces adjacent to each other in the insertion direction are pivotably connected together via two first mutually opposed rotation shafts in upward and downward directions and pivotably connected via two second mutually opposed rotation shafts at positions differing by 90° from the first rotation shafts in a circumferential direction of the bending pieces in leftward and rightward directions, and the passive bending portion has a configuration in which the bending pieces adjacent to each other in the insertion direction are pivotably connected together via two third mutually opposed rotation shafts located coaxially with the first rotation shafts in the insertion direction, pivotably connected together via two fourth mutually opposed rotation shafts located at positions differing by 60° from the third rotation shafts in the circumferential direction and pivotably connected together via two fifth mutually opposed rotation shafts located at positions differing by 60° from the third rotation shafts and the fourth rotation shafts in the circumferential direction wherein a maximum bending angle of the passive bending portion having three-axis bending capability is more than 30° and less than 90° over an entire circumference regardless of the bending direction, with a number of bending pieces, an interval between the bending pieces in the insertion direction and an angle between the bending pieces being set to predetermined values, and wherein a direction in which the bending angle of the passive bending portion having the three-axis bending capability becomes a maximum angle matches upward and downward directions in which the active bending portion bends, in a distribution of maximum bending angles in bending directions of the passive bending portion over the entire circumference based on combination of a two-axis bending configuration by the active bending portion and a three-axis bending configuration by the passive bending portion.

* * * * *